(12) United States Patent
Maaskamp et al.

(10) Patent No.: US 9,072,582 B2
(45) Date of Patent: Jul. 7, 2015

(54) RECTOCELE DEVICE

(71) Applicants: Ryan Maaskamp, San Francisco, CA (US); Armand Maaskamp, Napa, CA (US); Gervasio Salgado, Marbella (ES)

(72) Inventors: Ryan Maaskamp, San Francisco, CA (US); Armand Maaskamp, Napa, CA (US); Gervasio Salgado, Marbella (ES)

( * ) Notice: Subject to any disclaimer, the term of this patent is extended or adjusted under 35 U.S.C. 154(b) by 239 days.

(21) Appl. No.: 13/803,890

(22) Filed: Mar. 14, 2013

(65) Prior Publication Data
US 2014/0275749 A1   Sep. 18, 2014

(51) Int. Cl.
*A61F 2/00* (2006.01)

(52) U.S. Cl.
CPC ............. *A61F 2/0027* (2013.01); *A61F 2/0022* (2013.01)

(58) Field of Classification Search
CPC ... A61F 2/0004; A61F 2/0009; A61F 2/0013; A61F 2/0022; A61F 2/0027
USPC ............... 600/29–32, 37, 184, 201, 207, 210; 606/205–207
See application file for complete search history.

(56) References Cited

U.S. PATENT DOCUMENTS

| | | | |
|---|---|---|---|
| 860,591 A | 7/1907 | Baird |
| 2,400,251 A | 5/1946 | Nagel |
| 2,494,393 A | 1/1950 | Lamson |
| 2,856,920 A | 10/1958 | Indelicato |
| 3,994,291 A | 11/1976 | Salmasian |
| 4,612,924 A | 9/1986 | Cimber |
| 4,669,478 A | 6/1987 | Robertson |
| 4,875,898 A | 10/1989 | Eakin |
| 4,920,986 A | 5/1990 | Biswas |
| 4,986,823 A | 1/1991 | Anderson |
| 5,364,146 A | 11/1994 | Brandorff |
| 5,603,685 A | 2/1997 | Tutrone, Jr. |
| 5,716,329 A | 2/1998 | Dieter |
| 5,988,169 A | 11/1999 | Anderson |
| 6,077,257 A | 6/2000 | Edwards |
| 6,168,586 B1 | 1/2001 | Hahnen |
| 6,676,594 B1 | 1/2004 | Zunker |
| 6,795,737 B2 | 9/2004 | Gielen |
| 7,179,219 B2 | 2/2007 | Matlock |
| 7,288,063 B2 | 10/2007 | Petros |
| 7,325,546 B2 | 2/2008 | Burbank |
| 7,513,868 B1 | 4/2009 | Fontenot |
| 7,634,049 B2 | 12/2009 | Galkin |
| 7,771,344 B2 | 8/2010 | Ziv |
| 7,981,024 B2 | 7/2011 | Levy |
| 8,302,608 B2 | 11/2012 | Harmanli |
| 8,360,954 B2 | 1/2013 | Kim |
| 2003/0078526 A1 | 4/2003 | Farley |
| 2005/0021080 A1 | 1/2005 | Feuer et al. |
| 2006/0025782 A1 | 2/2006 | Klein et al. |
| 2006/0211911 A1 | 9/2006 | Jao et al. |
| 2009/0216071 A1 | 8/2009 | Zipper |
| 2010/0174214 A1 | 7/2010 | Gabbay et al. |

FOREIGN PATENT DOCUMENTS

| | | |
|---|---|---|
| EP | 0700669 A1 | 3/1996 |
| FR | 2228464 83 | 4/1976 |

*Primary Examiner* — John Lacyk
(74) *Attorney, Agent, or Firm* — Kenneth Altshuler (57) ABSTRACT

A stool evacuate assist device to address rectocele disorder is described. The device generally comprises a handle and a paddle wherein the handle and the paddle are delineated by a bend in the device. The stool evacuation device further has an expandable sheath located on the paddle that after being inserted in a vagina of a woman and after being expanded in the vagina, the expandable sheath is in contact with a rectovaginal wall of the vagina. The handle is adapted to translate directional pressure on the rectovaginal wall via the expandable sheath when manipulated by the woman. The bend between the handle and the paddle essentially remains outside of the vagina when the expandable sheath is expanded in the vagina.

22 Claims, 9 Drawing Sheets

RECTOCELE DEVICE

CROSS-REFERENCE TO RELATED APPLICATIONS

None

FIELD OF THE INVENTION

The present invention is directed to a rectocele device that is useful in reducing the effects of a rectocele which impair a woman's ability to move bowel.

BACKGROUND OF THE INVENTION

Figure 1:
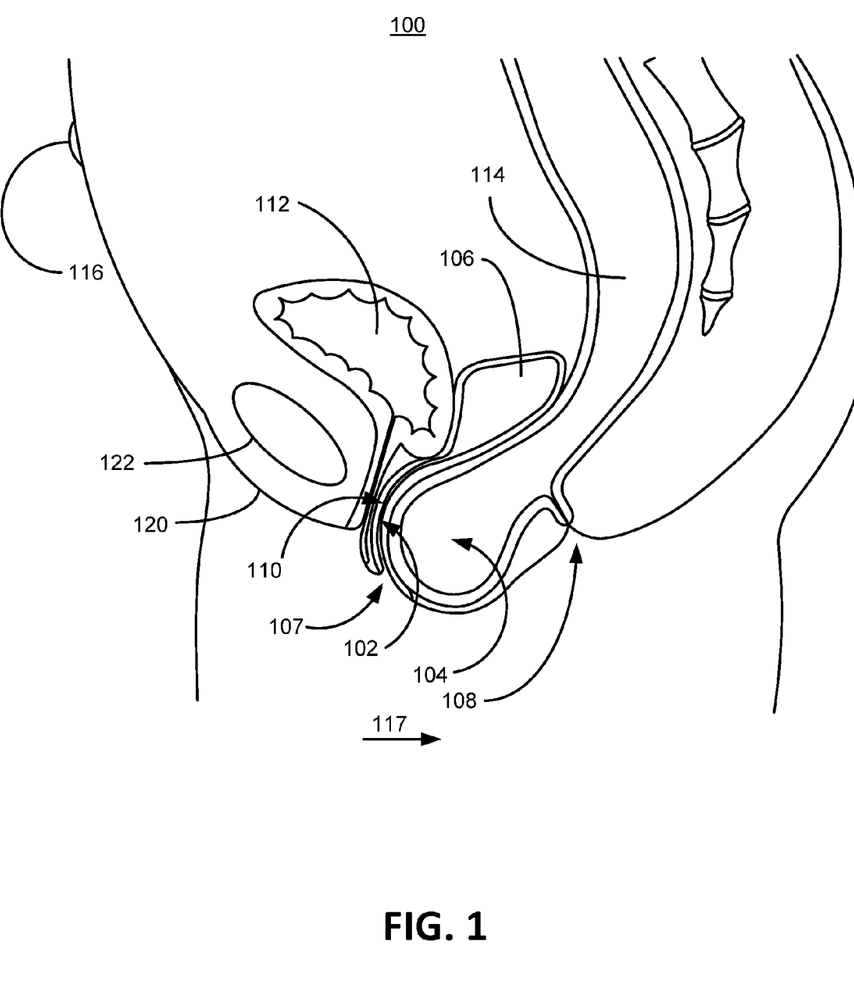
FIG. 1 depicts a cross section of a pelvic area of a woman suffering from a rectocele.

Rectocele in a woman is a condition whereby the woman's rectum is prolapsed into the posterior wall of the woman's vagina. Rectocele is defined as bulging of the front wall of the rectum (rectovaginal wall) into the vagina. Rectocele is due to weakening of the pelvic support structures and thinning of the rectovaginal wall (the tissues separating the rectum from the vagina) and is primarily believed to be a result of childbirth, chronic constipation, and hysterectomy. The rectum ballooning into the vagina often is exacerbated during a bowel movement as shown in FIG. 1. As a result, the woman may experience the sensation of pressure or protrusion within the vagina, and the occasional feeling that the rectum has not been completely emptied after a bowel movement. In more moderate cases, a woman may have difficulty passing stool because the attempt to evacuate pushes the stool into the rectocele instead of out through the anus.

In an attempt to aid with a bowel movement in cases of rectocele, a woman may insert her fingers into her vagina to manually press against the rectocele, which helps create a uniform pathway for stool to move out of the rectum. Because a rectocele may protrude to the right of left of the posterior wall of the vagina, by using the sense of touch in her fingers, a woman is able to reposition her fingers to the where the rectocele occurs. In other words, a woman is able to press against the rectocele with her fingers by taking advantage of bio-feedback in her fingers.

Though surgical procedures exist to repair rectoceles, in less severe cases, a number of optional devices currently exist to provide some rectocele relief. One family of devices includes spoon-like devices, which are used just prior to a bowel movement to essentially when the bowel is completed. Unlike the biofeedback of fingers to facilitate repositioning of pressure against the rectocele, spoon-like devices are unable to sense if a rectocele is sliding to the right or left of the spoon. When a rectocele slides to the right or left of the spoon, the woman may press harder against her posterior rectovaginal wall with the spoon because she is not experiencing proper stool evacuation and cannot sense through bio-feedback that the rectocele has moved around the spoon, which then may cause damage to her posterior rectovaginal wall.

Another family of devices used to address rectoceles includes pessaries, which are typically inflated balloons that provide static pressure on all surfaces of the vaginal canal (the rectovaginal wall, lateral walls and the bladdervaginal wall). Pessaries offer extended support to address rectoceles. Pessaries are not inserted into a vagina just prior to a bowel movement to the point of when a bowel movement is complete. Rather, pessaries are left in the vagina for an extended period of time, sometimes being inserted in the morning and removed at night to being left in for days at a time, if not longer.

It is to innovations related to addressing passing a bowel movement in women suffering from a rectocele that the claimed invention is generally directed.

SUMMARY OF THE INVENTION

The present invention is directed to a rectocele device that is useful in providing pressure against the rectocele to improve bowel movements in women.

Embodiment of the present invention can therefore comprise a rectocele device comprising: a handle; a paddle, wherein the handle and the paddle are distinguished by a bend in the rectocele device which forms essentially an L-shaped unit; an expandable sheath located on the paddle that after being inserted in a vagina of a woman and is expanded is in contact with a rectovaginal wall of the vagina, the handle, which remains outside of the vagina, adapted to translate directional pressure on the rectovaginal wall via the paddle when the handle is in manually pulled towards a belly button associated with the woman.

Another embodiment of the present invention can therefore comprise a stool evacuate assist device comprising: a handle and a paddle, the handle and the paddle are delineated by a bend in the device; an expandable sheath located on the paddle that after being inserted in a vagina of a woman and after being expanded in the vagina, the expandable sheath is in contact with a rectovaginal wall of the vagina but is not in contact with a bladder-vaginal wall of the vagina, the handle adapted to translate directional pressure on the rectovaginal wall via the expandable sheath when manipulated by the woman, the bend essentially remains outside of the vagina when the expandable sheath is expanded in the vagina.

Yet another embodiment of the present invention can therefore comprise a rectocele device for assisting a woman to defecate, the rectocele device comprising: a handle; a paddle, wherein the handle is defined from the paddle by a bend in the rectocele device; an expandable mechanism located on the paddle that after being inserted in a vagina of a woman applies pressure on a rectovaginal wall of the vagina when expanded therein; and means for providing directional pressure on the rectovaginal wall.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving holding back rectoceles.

To illustrate an exemplary environment in which preferred embodiments of the present invention can be practiced, FIG. 1 depicts a cross section of a pelvic area of a woman 100 suffering from a rectocele 104. The rectocele 104 is shown bulging into the rectovaginal wall 102 of the vagina 106. The rectovaginal wall 102 is the septum between the vaginal vault (vagina) 106 and the rectal vault (rectum) 114 in the posterior direction 117 of the vagina 106. For reference, also shown herein are the bladder 112, the bladdervaginal wall 110, the vaginal opening 107, and the anus 108. Though not shown, the vagina 106 also has lateral walls of the vagina 106, which directionally extend towards the inner thighs of the woman 100. In other words, the rectovaginal wall 102 extends towards the posterior 117 and the bladdervaginal wall extends towards the anterior (pubic bone 122) of the woman 100, whereas, the lateral walls of the vagina 106 are orthogonal to the anterior/posterior direction. From the anterior side, also shown are the belly button 116, the pubic bone 122, and the mons veneris 120.

Figure 2:
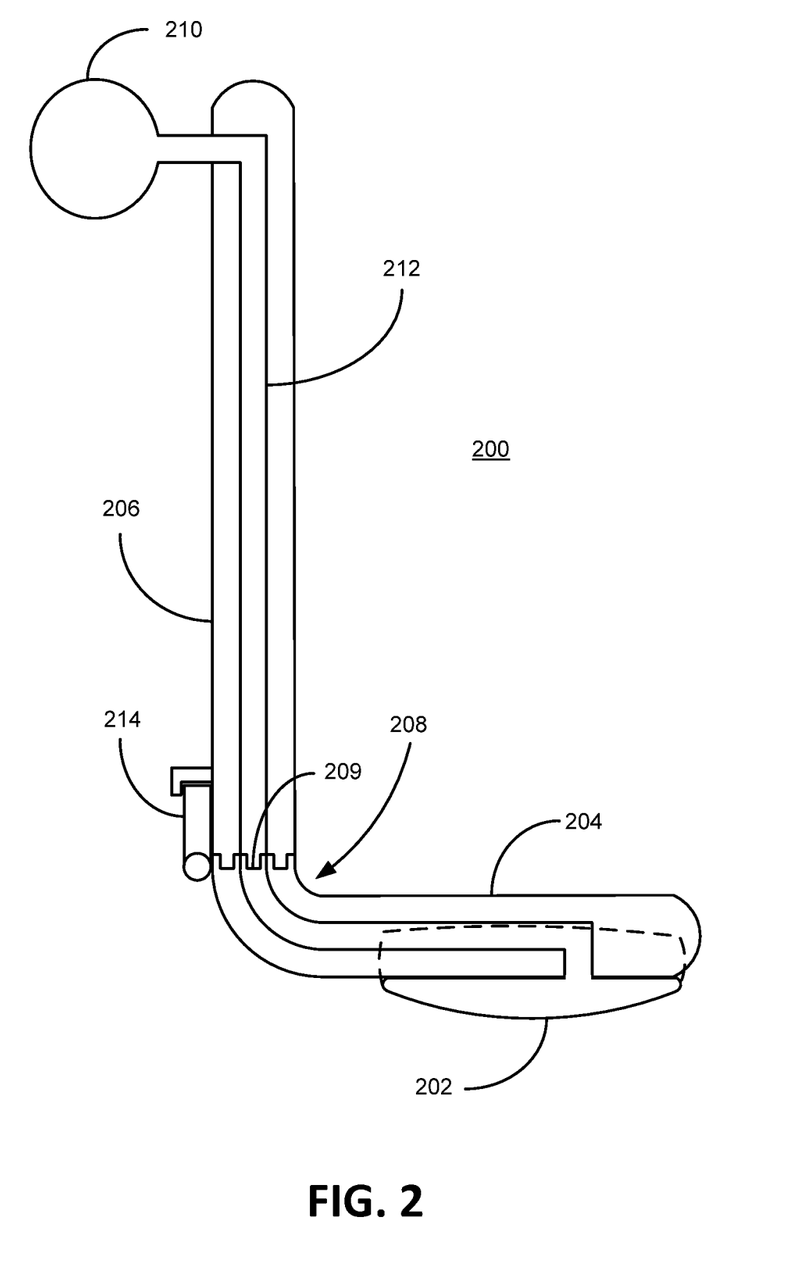
FIG. 2 depicts an embodiment of a rectocele device adapted to mechanically reduce the bulge of the rectocele during a bowel movement, consistent with embodiments of the present invention.

Consistent with embodiments of the present invention, FIG. 2 depicts an embodiment of a rectocele device 200 adapted to mechanically reduce the bulge of the rectocele 104 during a bowel movement. More specifically, the rectocele device 200 generally comprises a handle 206 that is integrated with a paddle 204 whereby the paddle 204 and the handle 206 are distinguished by a bend 208 in the rectocele device 200. In other words, the paddle 204 is essentially defined at the bend location 208 in the rectocele device 200. In the present illustrative embodiment, the rectocele device 200 is essentially an L-shaped unit (bend at 90 degrees) comprising the paddle 204 and the handle 206, though other embodiments contemplate a bend different from 90 degrees. An expandable sheath 202 is located on the paddle 204 and, in one embodiment, is expanded by an inflation means that expands a uniform sheath 202 into a non-uniform shape. In the present embodiment, the expandable sheath 202 is contemplated to be made out of silicone (or some other stretchable material). Other embodiments contemplate a mechanical expansion mechanism to expand the expandable sheath 202. In the depicted embodiment, the expandable sheath 202 is essentially inflated via a balloon catheter system disposed inside of the expandable sheath 202, which is inflated by compressing an inflation bulb 210 located at or near the end of the handle 206. Air, or some other comparable fluid or gel able to accomplish similar effects, flows through a tube 212 that is connected to the expandable sheath 202 and the inflation bulb 210. In this embodiment, the expansion sheath 202, the inflation bulb 210 and the tube 212 essentially maintain a constant volume of air, or comparable fluid, such that when the inflation bulb 210 is squeezed, the expandable sheath 202 expands. Other inflation means contemplated include a spring loaded push-button system that is finger activated (not shown), whereby a finger pushes down on a vertical rod that depresses the inflation bulb 210, filling a balloon in the expandable sheath 202 with air, thus expanding the expandable sheath 202. Yet another embodiment contemplates a compressed air cartridge, such as a $CO_2$ cartridge, that can be activated, such as by a push button, to inflate the expandable sheath 202 with a release valve to decompress the expandable sheath 202. Other embodiments contemplate an electrically powered pump inflating a balloon that expands the expandable sheath 202. The preceding embodiments for inflating a balloon disposed inside of the expandable sheath 202 are by way of example and are not limiting to the optional means of inflation within the scope and spirit of the present invention. Hence, there are a variety of ways to expand the expandable sheath 202, which are within possession and knowledge of a skilled artisan.

Certain embodiments contemplate the rectocele device 200 being used essentially from just prior to a bowel movement of a woman to just after the bowel movement of the woman. By using the rectocele device 200 for essentially just a bowel movement, a woman can live free from a foreign object in her vagina 106 during her normal daily activities. Hence, when a woman needs to move stool, she inserts the paddle 204 in her vagina 106 and expands the expandable sheath 202, such as, for example, by squeezing the air out of the inflation bulb 210. The expandable sheath when expanded is in contact with the woman's rectovaginal wall 102. During operation, the handle 206 remains outside of the vagina 106 at essentially where the bend 208 is located. The handle 206 translates directional pressure on the rectovaginal wall 102 by way of the paddle 204 when the handle 206 is in manually pulled towards the woman's belly button 116. More specifically, the handle 206 is used as a lever rotating about the mons veneris 120, thus pushing back the rectocele 104 by way of the paddle 204 and expandable sheath 202 pushing against the rectovaginal wall 102. When the woman has completed moving stool, she contracts the expandable sheath 202, such as, for example, by releasing the inflation bulb 210, and withdraws the paddle 204 from her vagina 106.

Certain embodiments contemplate the expandable sheath 202 being in contact with the rectovaginal wall 102 and lateral walls (not shown) of the vagina 106, but not in contact with the bladdervaginal wall 110. By being in contact with the at least a portion of the lateral walls of the vagina 106 and the rectovaginal wall 102, the expandable sheath 202 helps control the rectocele 104 from sliding around the side of (to the right or left) the paddle 204. Accordingly, the rectocele 104 is adequately compressed to allow the stool to evacuate effectively with the rectocele device 200.

Also, depicted in FIG. 2 is an embodiment where the paddle 204 is removable from the handle 206 via a joint 209. Advantages of the paddle 204 being removed from the handle 206 includes the option for a disposable paddle 204, or a paddle 204 that is potentially more easily cleaned. The paddle 204 can be removed from the handle 206 via a latching mechanism 214, shown herein. The joint 209 and latching mechanism 214 are an embodiment illustrating a removable paddle 204 and is not intended to be limiting to optional ways to accomplish providing a removable paddle 204 within the scope and spirit of the present invention.

Figure 3:
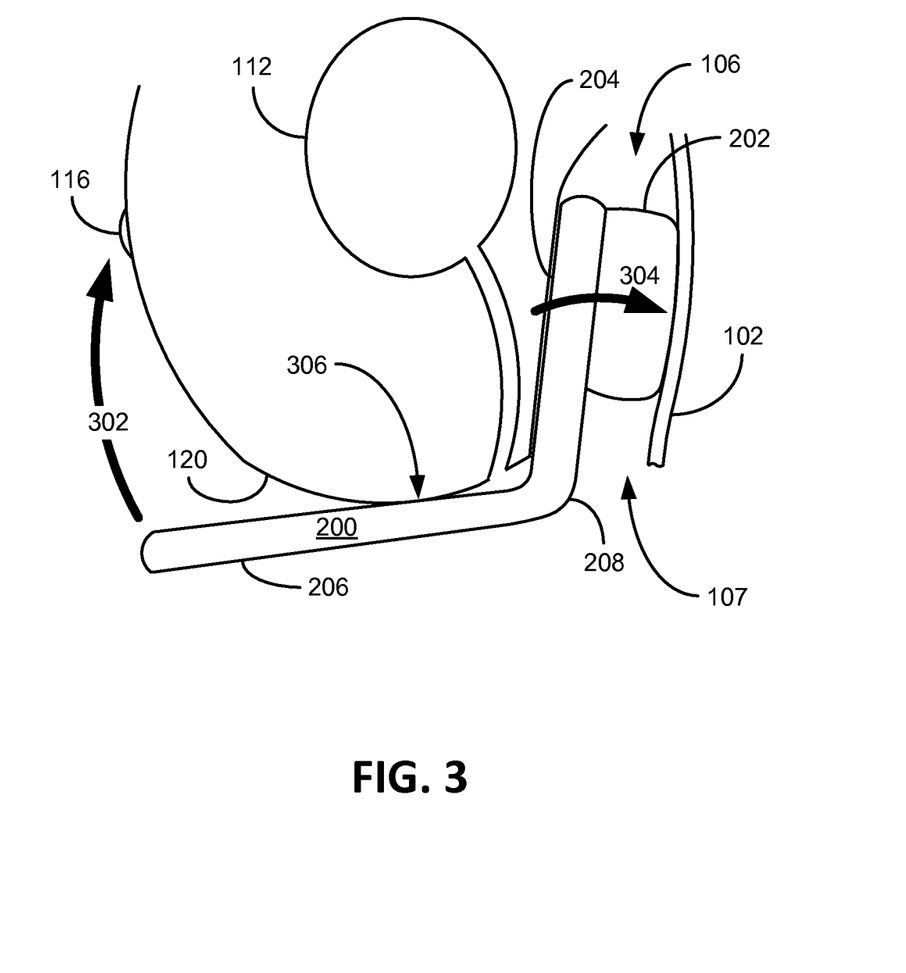
FIG. 3 depicts a rectocele device being used to press against a rectocele, consistent with embodiments of the present invention.

FIG. 3 depicts a rectocele device 200, consistent with embodiments of the present invention, being used to press against a rectocele 104. As illustratively shown, the paddle 204 is located in the vagina 106 and the expandable sheath 202 is expanded and pressing against the rectovaginal wall 102 in the direction shown by arrow 304. The handle 206 is being pulled towards the belly button 116 as indicated by the arrow 302, which pivots the rectocele device 200 about the pivot point 306 on the mons veneris 120. As shown, the bend 208 is essentially outside of the vaginal opening 107. Also, in this embodiment, the expandable sheath 202 does not contact the bladdervaginal wall 110. However, optional embodiments contemplate an expandable sheath additionally contacting the bladdervaginal wall 110.

Figure 4:
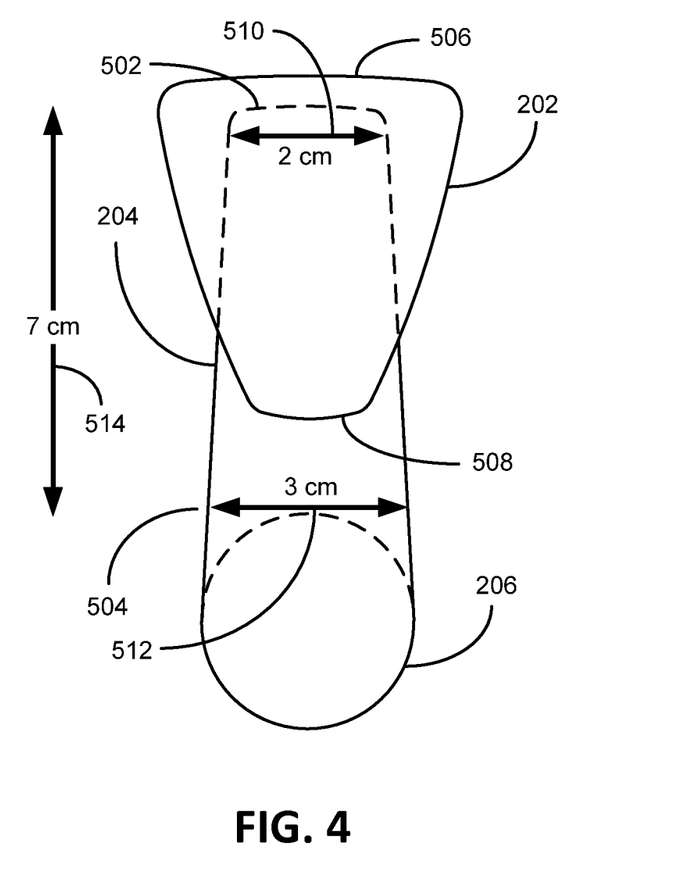
FIG. 4 illustratively shows a view of the expandable sheath that contacts the rectovaginal wall when expanded, consistent with embodiments of the present invention.

FIG. 4 shows a view of the expandable sheath 202 that contacts the rectovaginal wall 102 when expanded. As illustratively shown, the present embodiment depicts the expandable sheath 202 possessing a non-uniform shape when expanded. More specifically, the expandable sheath 202 possesses a wide top end 506 and a narrow bottom end 508 because the vaginal vault 106 naturally accommodates this shape well. Also as illustratively shown, the paddle 204 is tapered such that the top end 502 is narrower than the paddle bottom end 504 to improve insertion into the vagina 106. One embodiment contemplates the paddle top end 502 to be approximately 2 cm in width and the bottom to be approximately 3 cm in width. Certain embodiments further contemplate the paddle length to be between 4 cm and 9 cm in length, but preferably 7.5 cm in length.

Figure 5:
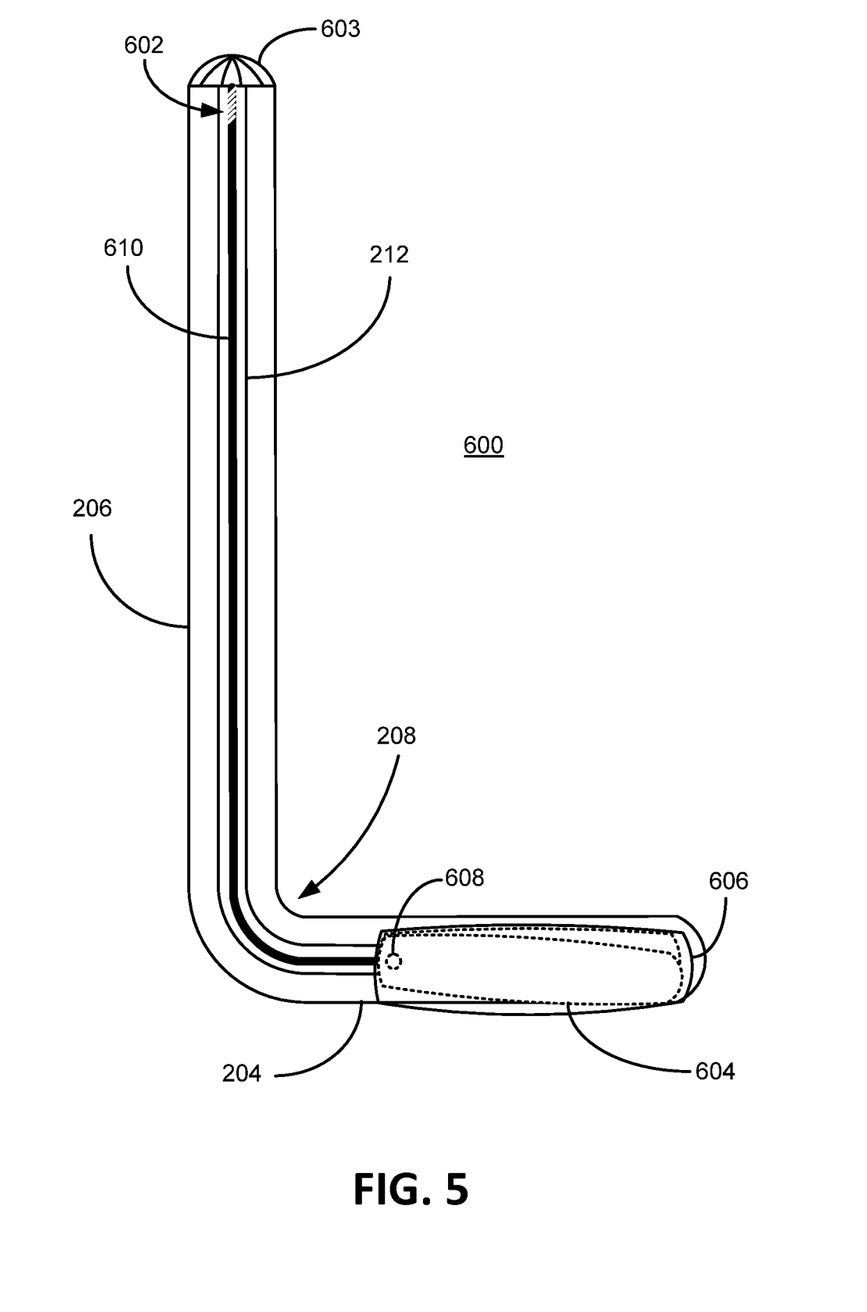
FIG. 5 shows an optional embodiment of an expandable sheath that is expanded by a mechanical hardware, consistent with embodiments of the present invention.
Figure 6A:
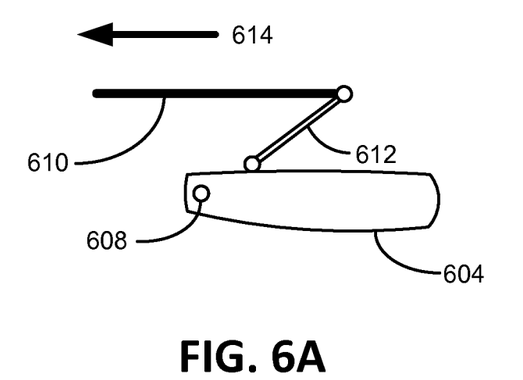
FIGS. 6A-6D illustratively depicts and embodiment of mechanical hardware adapted to expand an expandable sheath, consistent with embodiments of the present invention.
Figure 6B:
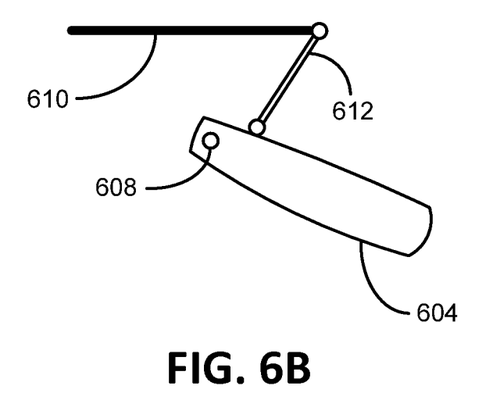
Figure 6C:
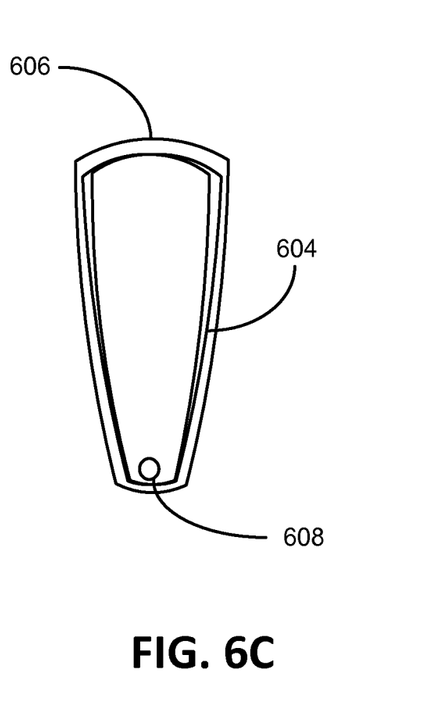
Figure 6D:
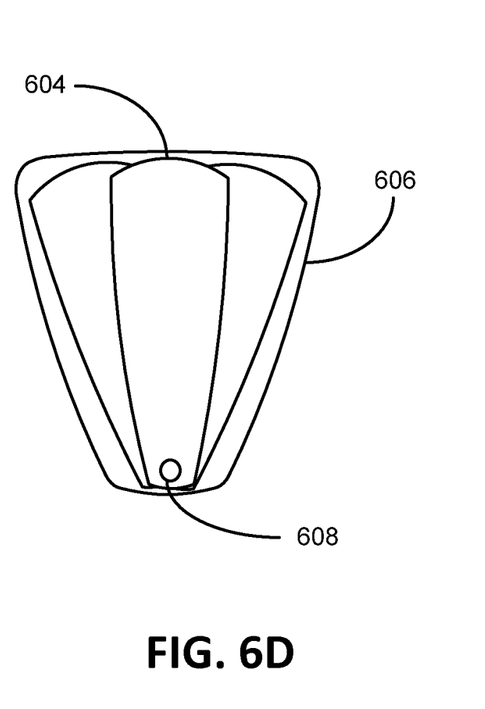

FIG. 5, as shown in conjunction with FIGS. 6A-6D, shows an optional embodiment wherein the expandable sheath 606 is expanded by mechanical hardware, consistent with embodiments of the present invention. With reference to FIG. 5, the expandable sheath 606 is disposed on the paddle 204 of the rectocele device 600. Here, the uniform shaped sheath 606 is not expanded. Contained inside the expandable sheath 606 is hardware, such as blades 604 that may be mechanically expanded by way of a knob 603 located at the end of the handle 206. In conjunction with FIGS. 6A and 6B, as the knob 603 is rotated, a threaded end 602 of a flexible rod 610 coupled with a captured bolt (not shown) in the knob 603 pulls the flexible rod 610 into the knob 603, directionally shown by arrow 614, which directionally rotates the blade about a pivot point 608 via a linking arm 612, for example. In this way, the blades 604 move from a retracted position, shown in FIG. 6C, to an expanded position, shown in FIG. 6D, thus expanding the sheath 606 as shown. It should be appreciated that the illustrated embodiment of the mechanically expanding sheath is by way of example and is not limiting to other engineering designs to mechanically accomplish expanding the flexible sheath 606 within the scope and spirit of the present invention.

Figure 7A:
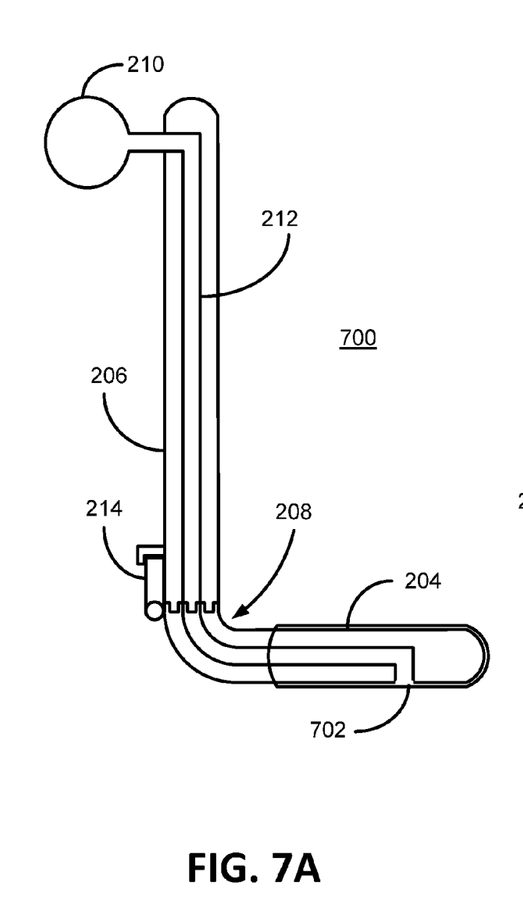
FIGS. 7A and 7B depict an alternative embodiment of a rectocele device, consistent with embodiments of the present invention.
Figure 7B:
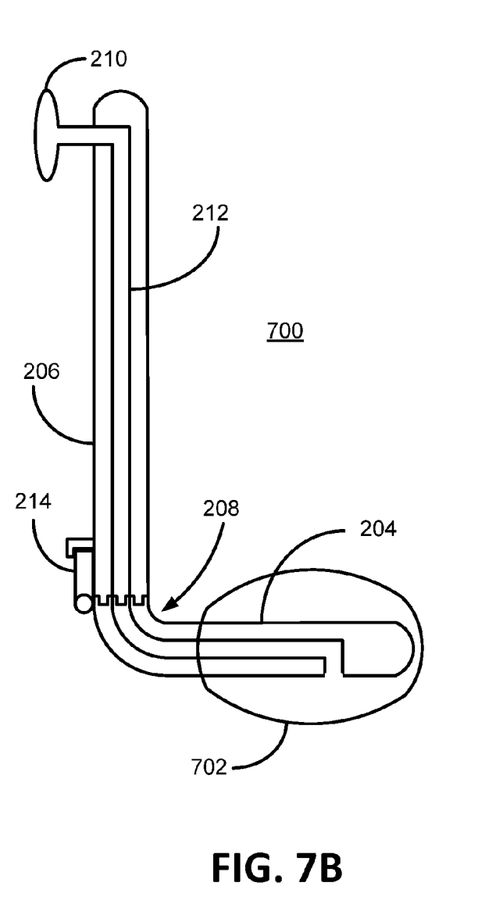

FIGS. 7A and 7B depict an alternative embodiment of a rectocele device 700, consistent with embodiments of the present invention. As illustratively shown in FIG. 7B, the paddle 204 possesses an expandable sheath 702 that essentially expands around the circumference of the paddle 204, which when inserted and expanded in a vagina 106 contacts the rectovaginal wall 102, the bladder vaginal wall 110 and the lateral vaginal walls of the vagina. FIG. 7A illustratively shows that the expandable sheath 702 is in a non-expanded state whereby the inflation bulb 210 is expanded. FIG. 7B illustratively shows the expandable sheath 702 is in an expanded state whereby the inflation bulb 210 is compressed.

Figure 8:
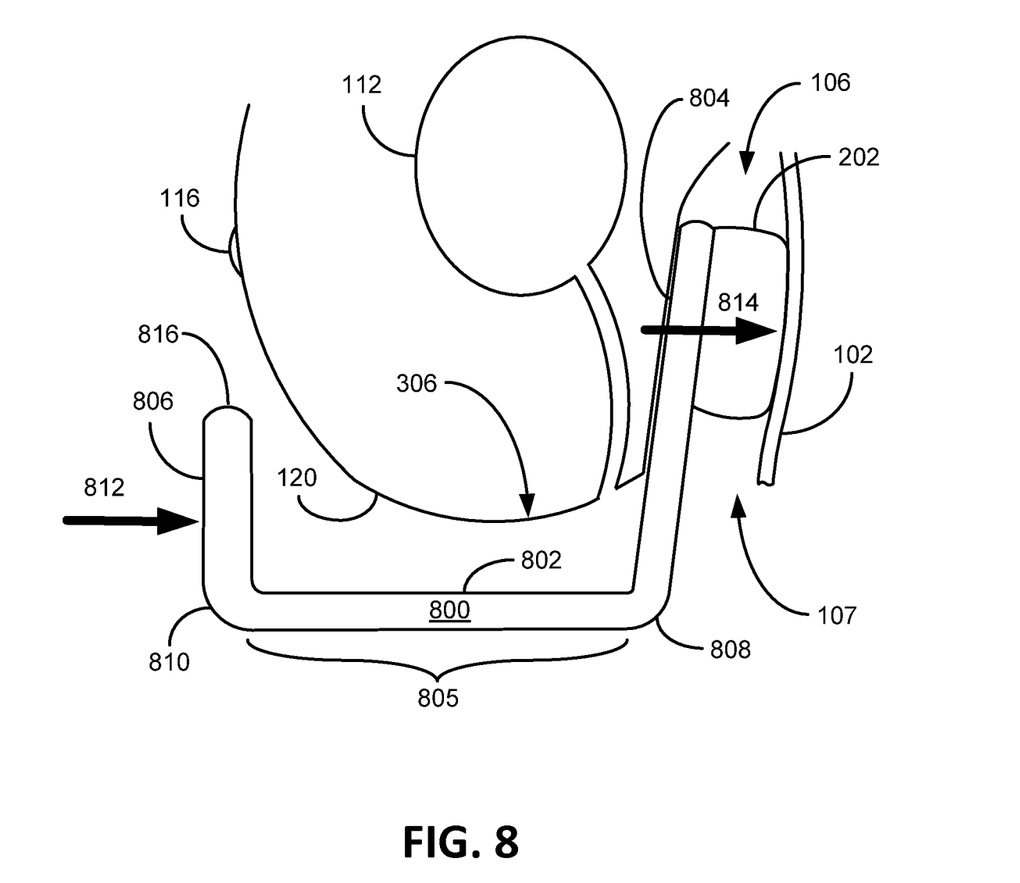
FIG. 8 depicts yet another alternative embodiment of a rectocele device, consistent with the present invention.

FIG. 8 depicts yet another alternative embodiment of a rectocele device 800, consistent with the present invention. As illustratively shown, the paddle 804 is located in the vagina 106 and the expandable sheath 202 is expanded and pressing against the rectovaginal wall 102 in the direction shown by arrow 814. The handle 802 is defined from the paddle 804 by a first bend 808, which is just outside of the vaginal opening 107. The handle 802 further comprises a grip 806 which is defined by a second bend 810 and the distal end of the handle 816. For reference, the handle 802 possesses a mid-handle portion 805 between the first bend 808 and the second bend 810. In this embodiment, when the grip 806 is pressed towards the posterior direction 812, the expandable sheath 202 operably pushes (arrow 814) against the rectovaginal wall 102, thus addressing the rectocele 104. Though one embodiment contemplates the first bend 808 being essentially 90 degrees between the mid-handle portion 805 and the paddle 804 and the second bend 810 being essentially 90 degrees between the mid-handle portion 805 and the grip 806, other embodiments contemplate the bends 808 and 810 being different angles greater than 45 degrees and less than 135 degrees for example.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, additional expansion elements/devices to expand the expandable sheath can be used in a consistent manner with embodiments of the present invention while still maintaining substantially the same functionality without departing from the scope and spirit of the present invention. Another example can include various additional devices (manual, motorize, pneumatic, etc) used to expand or contract the expandable sheath without departing from the scope and spirit of the present invention. Yet, other embodiments can include multiple sheaths to accomplish the end result without departing from the scope and spirit of the present invention. The preferred embodiments described herein are directed to a rectocele device, which accordingly is not intended for uses beyond the scope and spirit of addressing a rectocele of a woman.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed.

What is claimed is:

1. A rectocele device comprising:
   a handle;
   a paddle wherein the handle and the paddle are distinguished by a bend in the rectocele device which forms essentially an L-shaped unit; and
   an expandable sheath located on the paddle that is adapted to be expanded in a vagina of a woman after being inserted therein, the woman having a posterior side and an anterior side, the expandable sheath further and adapted to be in contact with a rectovaginal wall of the vagina, the handle adapted to stay outside of the vagina and adapted to be held by the woman is configured to extend towards the anterior side of the woman when the paddle is disposed in the vagina.

2. The rectocele device of claim 1 wherein the rectocele device is configured to press against a stool of the woman via the rectovaginal wall.

3. The rectocele device of claim 1 further comprising an inflation bulb disposed on the handle that is connected to the expandable sheath by way of a tube.

4. The rectocele device of claim 1 further comprising an inflation bulb disposed on the handle that is connected to the expandable sheath by way of a tube wherein the inflation bulb, the expandable sheath and the tube essentially maintain a constant amount of gas.

5. The rectocele device of claim 4 wherein the expandable sheath expands when the inflation bulb is manually squeezed.

6. The rectocele device of claim 1 wherein the L-shaped unit possesses an angle that is essentially ninety degrees between the handle and the paddle.

7. The rectocele device of claim 1 wherein the paddle possesses a distal end that is tapered so that the distal end is smaller than where the paddle meets the handle at the bend in the L-shaped unit.

8. The rectocele device of claim 1 wherein the expandable sheath is expanded by way of inflation and deflation via of an electrically powered pneumatic device.

9. The rectocele device of claim 1 wherein the expandable sheath extends at least to the distal end of the paddle.

10. The rectocele device of claim 1 wherein the expandable sheath when expanded is further adapted to contact both lateral sides of the vagina, but not a bladder-vaginal wall of the vagina.

11. The rectocele device of claim 1 wherein the expandable sheath is expanded by mechanical hardware within the sheath.

12. The rectocele device of claim 11 wherein the expandable sheath is adapted to be manually expanded and contracted.

13. The rectocele device of claim 1 wherein the handle is detachable from the paddle.

14. A stool evacuate assist device comprising:
a handle and a paddle, the handle and the paddle are delineated by a bend in the device; and
an expandable sheath located on the paddle, the paddle and expandable sheath adapted to being inserted in a vagina of a woman the expandable sheath is adapted to be in contact with a rectovaginal wall of the vagina when expanded in the vagina, but is not adapted to be in contact with a bladder-vaginal wall of the vagina, the handle adapted to translate directional pressure on the rectovaginal wall via the expandable sheath when manipulated by the woman, the bend essentially adapted to remain outside of the vagina when the expandable sheath is expanded in the vagina.

15. The stool evacuation assist device of claim 14 wherein the expandable sheath is expanded by a mechanical linkage.

16. The stool evacuation assist device of claim 14 wherein the expandable sheath is expanded by inflating the sheath with fluid.

17. The stool evacuation assist device of claim 14 wherein the handle and the paddle forms essentially an L-shaped unit.

18. The stool evacuation assist device of claim 14 further comprising a grip defined by a second bend in the handle wherein the handle is adapted to be manipulated by the woman in a posterior direction wherein the directional pressure is translated on the rectovaginal wall via the expandable sheath.

19. The stool evacuation assist device of claim 14 wherein the handle extends towards a belly button associated with the woman when the paddle is inserted in the vagina.

20. A method for assisting a woman to defecate using a rectocele device, the method comprising:
providing a device with a handle,
a paddle, the handle is defined from the paddle by a bend in the rectocele device, and
an expandable mechanism located on the paddle;
grasping the handle;
inserting the paddle through a vaginal opening in a vagina of the woman by the woman before the woman has a bowel movement, the handle extending towards a front side of the woman;
expanding the expandable mechanism inside of the vagina;
manipulating the handle to apply pressure on a rectovaginal wall of the vagina during the bowel movement;
withdrawing the paddle from the vagina by the woman after the bowel movement.

21. The rectocele device of claim 20 wherein the expandable mechanism when expanded in the vagina does not expand in a direction where the handle extends and is essentially not in contact with a bladder-vaginal wall of the vagina.

22. The rectocele device of claim 14 wherein the woman possesses an anterior side and a posterior side, the handle extending towards the anterior side of the woman when the paddle is inserted through a vaginal opening.

* * * * *